United States Patent [19]
Silver et al.

[11] Patent Number: 5,514,166
[45] Date of Patent: May 7, 1996

[54] DEVICE AND METHOD FOR SUPPORTING A BREAST SHIELD AND RELATED PUMP EQUIPMENT

[75] Inventors: Brian H. Silver; Gotthilf Weniger, both of Cary; Kathleen A. Lockridge; Richard S. Weston, both of Crystal Lake, all of Ill.

[73] Assignee: Medela, Inc., McHenry, Ill.

[21] Appl. No.: 375,977

[22] Filed: Jan. 20, 1995

[51] Int. Cl.[6] ................................................. A61M 1/06
[52] U.S. Cl. ................................ 604/74; 604/54; 450/36
[58] Field of Search ............................ 604/74, 75, 73; 128/890; 54/20, 58, 59; 450/36, 37

[56] References Cited

U.S. PATENT DOCUMENTS

| | | |
|---|---|---|
| 22,018 | 11/1958 | Davidson . |
| 22,080 | 11/1958 | Lewis . |
| D. 246,729 | 12/1977 | Murphy . |
| 2,054,491 | 9/1936 | Tynan . |
| 2,436,430 | 2/1948 | Hart . |
| 2,492,862 | 12/1949 | Harvey . |
| 2,495,307 | 1/1950 | Abramson . |
| 2,516,129 | 7/1950 | Leo et al. . |
| 2,585,338 | 7/1952 | Meares ............................. 450/36 |
| 2,748,771 | 6/1956 | Richards . |
| 2,764,759 | 10/1956 | Gazelle . |
| 3,757,784 | 9/1973 | Avery . |
| 4,270,538 | 6/1981 | Murphy . |
| 4,335,728 | 6/1982 | Fildan ............................. 450/36 |
| 4,566,458 | 1/1986 | Weinberg . |
| 4,640,287 | 2/1987 | Anderson et al. .............. 450/36 |
| 4,878,879 | 11/1989 | Kunstadter ..................... 450/36 |
| 5,032,103 | 7/1991 | Larsson . |
| 5,071,403 | 12/1991 | Larsson ........................... 604/74 |

FOREIGN PATENT DOCUMENTS

1159117  7/1969  United Kingdom .

*Primary Examiner*—C. Fred Rosenbaum
*Assistant Examiner*—Perry E. Van Over
*Attorney, Agent, or Firm*—Willian Brinks Hofer Gilson & Lione

[57] ABSTRACT

A device and method are provided for supporting a breast shield of a breast pump upon a woman's breast in a "hands-free" manner. Such a breast shield support includes, for example, a base member, such as a garment, that is adapted to be carried on a woman's torso. Part of the breast pump, such as the breast shield, is releasably attached to the base member and supports the breast shield on the exposed breast. Embodiments include corresponding fasteners on the breast shield and a brassiere, a harness-type strap arrangement for holding the shield against the breast and a breast shield which slips through a flap formed in a brassiere cup and is supported by the cup material.

55 Claims, 10 Drawing Sheets

DEVICE AND METHOD FOR SUPPORTING A BREAST SHIELD AND RELATED PUMP EQUIPMENT

BACKGROUND OF THE INVENTION

This invention relates generally to breast pumps, and more particularly to a device for supporting a breast shield, as well as related breast pump equipment, on a woman's breast.

Breast pumps for expressing and storing breast milk for later use are well known. Two types of breast pumps are generally available for use by nursing mothers: motor-driven pumps and manually-operated pumps. Typically, these breast pumps include a funnel-shaped shield or hood that fits over the nipple and a substantial portion of the breast, some type of vacuum pump (e.g., manually driven piston cylinder, squeeze bulb or electrically driven vacuum device) which is connected to the breast shield for generating an intermittent vacuum in the breast shield, and a container for the expressed breast milk. The intermittent suction generated by the vacuum pump within the breast shield causes a pulling or pressing of the breast, and is intended to mimic an infant's suckling action to thereby express milk from the breast. The expressed milk typically flows from the breast shield to the collection container for storage and subsequent use by the infant. The collection container, such as a small milk bottle, is ordinarily assembled in the breast shield as though an intermediate milk-directing channel and valve arrangement.

Brassieres, halter tops and other garments specifically designed for nursing mothers are also well known. Generally, these nursing brassieres include flaps which may be unfastened at one side from the brassiere to expose the breasts for nursing by an infant, or for enabling breast milk collection through pumping.

When desiring to use a breast pump to collect and store breast milk while wearing such a nursing brassiere or otherwise, a mother, after exposing the breast, holds the breast shield in position on the exposed breast. Obviously, depending on whether the breast pump is motor-driven or manually-operated, and further on whether one or two breast shields are being used at the same time, one or both of the mother's hands will be needed to perform the breast pumping operation. As can be readily seen, the nursing mother, whether at home or at work, will not have the use of at least one of her hands, such as to perform other tasks when she is using her breast pump. Therefore, it would be advantageous to develop a method and device that will permit a mother to use a breast pump while also allowing her the free use of her hands to perform other tasks.

SUMMARY OF THE INVENTION

It is a principal objective of the present invention to provide a device that supports a breast shield of a breast pump upon an exposed breast in a "hands-free" manner for the user. A related method is also provided. As hereinafter disclosed, the invention in its broadest sense contemplates any inanimate means whereby the breast shield is held in place on the breast without the need of the user or someone else to hold it in place. The breast shield support may be carried on the mother's body, or on a base which is movable to emplace the shield, or into which the mother can insert her breast(s).

In one aspect of the invention, such a support method and device contemplates a brassiere or other similar garment serving as a base, and a means for supporting the breast shield on the exposed breast associated with the base.

In one embodiment, the support means takes the form of a releasable fastener mechanism having interengaging fastener elements on a brassiere and on the breast shield. The brassiere has an aperture in the cup, such as provided by a flap, to expose the breast for emplacement of the breast shield of a breast pump. Corresponding fastener elements on the brassiere and breast shield are fastened together to support the breast shield on the exposed breast.

A variety of fastening mechanisms can be employed. For example, a removably mounted harness for the breast shield has straps which are releasably fastened to the brassiere/base, as by hooks, buttons, snaps and the like. In another embodiment, a band surrounding the perimeter of the breast shield carries fasteners which attach to the brassiere. In still another embodiment, part of the fastening mechanism is integrally formed with the breast shield.

According to another embodiment of the present invention, the support means takes the form of a flap and flap opening found in a brassiere-type garment specifically adapted to hold the breast shield in place. For example, the opening provided by the flap is of a smaller diameter in at least one dimension than the breast shield. The breast shield is inserted and slidably received through the opening, such that the breast shield is supported on the exposed breast between the breast and inner surface material of the brassiere. The flap can be reattached for further support of the shield. Alternatively, an adjustable strap can be additionally inserted which connects to a brassiere shoulder strap at one end and to the breast shield at the other end, to adjust the fit of and support the breast shield on the breast.

In a related embodiment, overlapped portions of material form the brassiere cup. The breast shield is inserted through the opening provided by the overlap, and then held in place on the breast by the brassiere cup material. In another related embodiment, the breast shield is provided with a teardrop-shaped rim, which increases the surface area of the breast shield and functions to better support the breast shield on the breast. The rim may be made releasably attachable to the shield. Moreover, the breast cup and the teardrop rim can further be provided with mating fastener elements to connect the breast shield to the breast cup.

In yet another related embodiment, the flap is unfastened from the brassiere to expose the breast and to allow the breast shield to be emplaced on the breast, and then reattached to the brassiere to support the breast shield on the breast. The flap may further be provided with a small aperture to accommodate a tubular extension of the breast shield, tubing or other breast pump equipment that extend from the breast shield.

In another aspect of the present invention, the breast shield support method and device utilizes a strap arrangement for supporting and holding the breast shield of a breast pump against the exposed breast. Preferably, the device is fashioned to hold two breast shields, each of which is supported by the a strap arrangement on a respective breast.

In one embodiment, the breast shield support device comprises a garment having one or more straps adapted to position the breast shield, and preferably to press it against the breast. Such a garment, for example, comprises a harness having a band portion adapted to wrap around the torso, and at least one strap adapted to support the breast shield on one of the woman's breasts. For example, a breast shield is held on the exposed breast by the strap engaging the breast pump on the outboard side of the shield, and holding the shield against the breast. In one such embodiment, the strap forms a loop within which the breast pump is supported with the shield held against the breast. The loop is attached to a base, such as a shoulder strap, at an upper part of the loop. Auxiliary straps connect the lower part of the loop to the torso band, to anchor and press the pump into position. A three-point adjustable anchoring arrangement for the harness is advantageously provided.

In another embodiment, the breast shield support device is adapted for use in a female athletic-type top, which has a waist-band portion and a brassiere portion. A breast shield supporting strap extends from the shoulder to the area of the breastbone, forming a loop to receive the breast shield. An auxiliary strap is advantageously provided to anchor the loop to the waist-band portion. A flap is formed in the cup of the brassiere portion to access the breast and the foregoing strap arrangement—which is located within the brassiere portion—for emplacement of the breast shield using the strap arrangement.

In yet another aspect of the invention, a device is provided wherein the breast shields are mounted for use, but which is not carried on the mother's person. For example, the breast shields are carried on a pumping mechanism in a manner whereby the mother simply inserts a breast into a respective shield. The pumping mechanism independently supports the shields.

The present invention permits a nursing mother, whether at home or at work, to use a breast pump to collect and store breast milk, while also providing her with free use of her hands. In addition, the present invention allows for hands-free "double pumping;" that is, using two breast shields to simultaneously express breast milk from both breasts. Also, the embodiments using straps and strap fasteners preferably employ adjustable straps to allow the mother to adjust the fit or tightness of the breast shield on the breast. Further, the present invention is easy to use and allows the breast shield to be quickly supported on the exposed breast.

These and other features and advantages of the present invention will be further understood upon consideration of the following detailed description of embodiments of the present invention, taken in conjunction with the accompanying drawings, in which:

DETAILED DESCRIPTION OF PRESENTLY PREFERRED EMBODIMENTS

Figure 15:
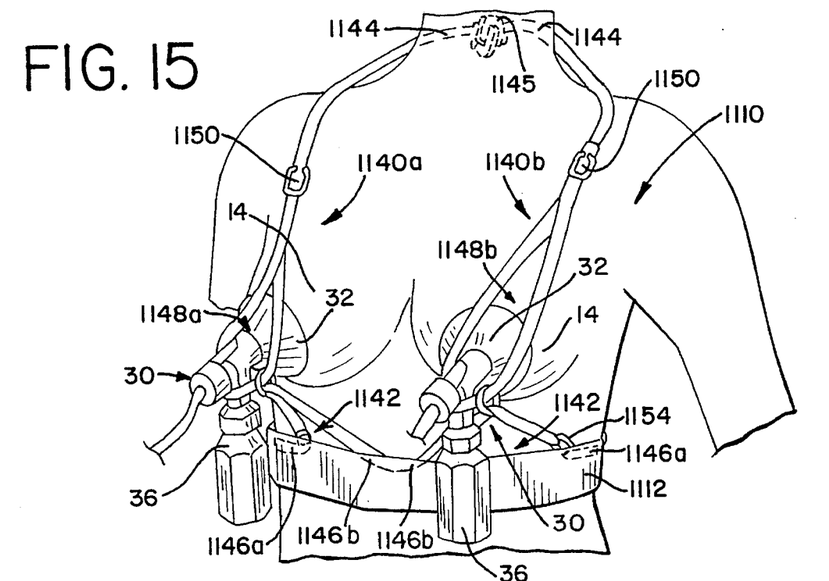
FIG. 15 is an operational view of an eleventh embodiment of a breast shield support of the present invention.

For ease of illustration, the present invention is generally shown and described below in terms of a single breast pump used for expressing breast milk from a single breast. However, as shown in FIG. 15 for example, it is specifically contemplated that the present invention is usable to simultaneously support a breast shield on each of a woman's breasts for breast milk collection. In addition, like numerals will be used to designate like elements in the respective embodiments of the present invention.

Figures 1, 2:
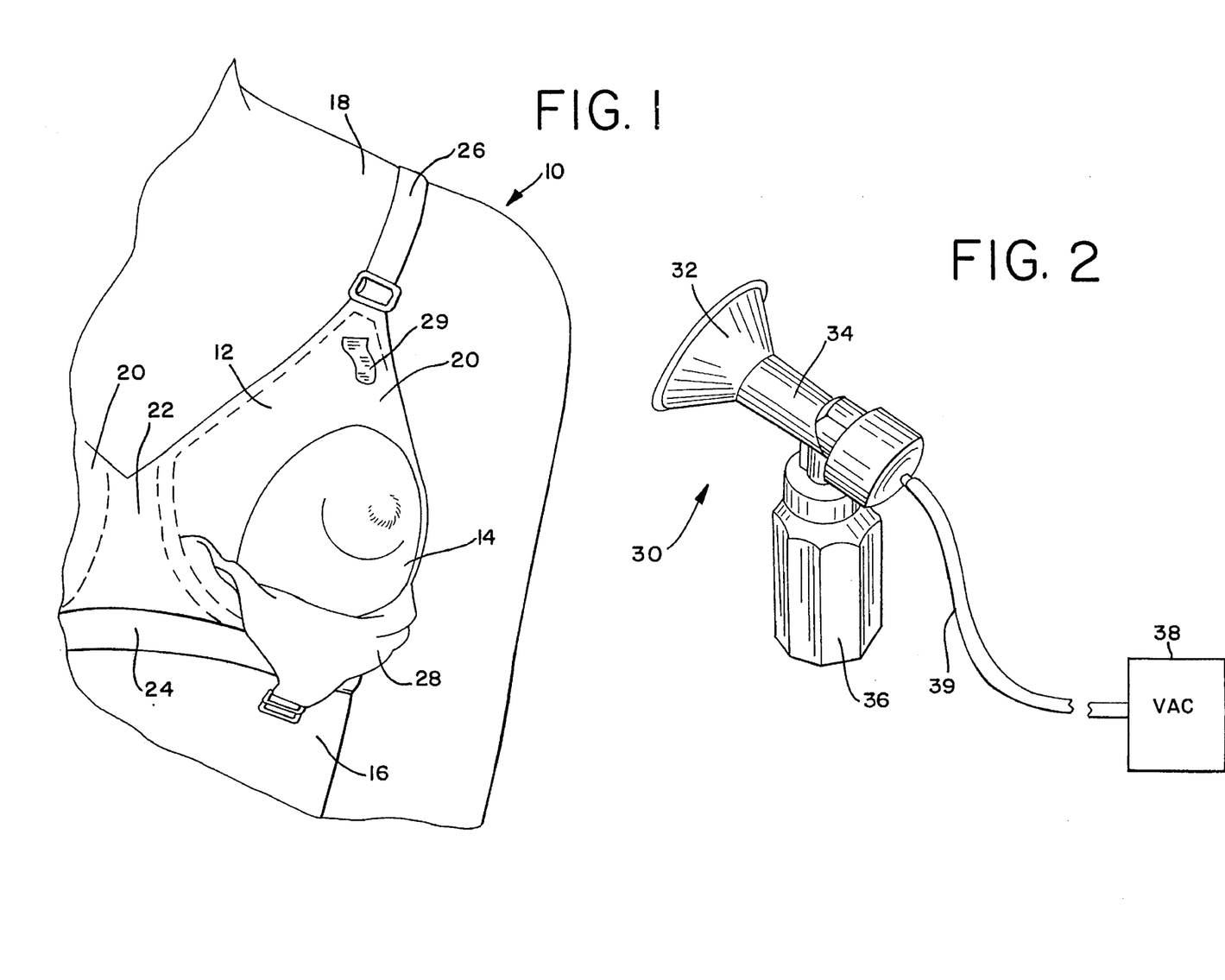
FIG. 1 is a perspective view of a brassiere in use showing the flap of the brassiere in an unfastened mode to expose the breast for nursing or breast pumping.
FIG. 2 is a perspective view of a representative breast pump assembly.

Turning now to the drawings, FIG. 1 shows a partial view of a woman 10 wearing a brassiere 12. The brassiere 12 is adapted to conform around the breasts 14, torso 16 and shoulders 18 of the woman 10 to support the breasts 14. The brassiere 12 includes two breast cups 20 interconnected by a connecting band 22, a torso band 24 having two ends (not shown) which extend around and are connected at the woman's back, and shoulder straps 26 (one of which is not shown) which are disposed between the respective breast cups 20 and the ends of the torso band 24. To the foregoing extent, the brassiere 12 is conventional.

Even though the present invention is shown and described herein in terms of the brassiere 12 shown in FIG. 1, it is specifically contemplated that other types of brassieres, for example strapless brassieres, and other types of breast support garments, including halter tops, camisoles, and the like may be used with the present invention, as will hereinafter be further understood.

As shown in FIG. 1, each of the breast cups 20 includes a flap 28 connected to the brassiere 12 near the bottom of the respective breast cup 20. The flap 28 is detachably connected to the brassiere 12 at a position near the respective shoulder straps 26 by a short strap 29. The flap 28 is oriented on the brassiere 12 such that it exposes the breast 14 for nursing or breast pumping as it is moved from the shoulder 18 to the torso 16. The flap 28 may be connected to the brassiere 12 in any suitable manner or orientation to expose the breasts 14.

A representative breast pump 30 for use with the present invention is shown in FIG. 2. The breast pump 30 includes a breast shield or hood 32 adapted to receive at least the nipple and some of the adjacent breast. The breast shield 32 receives the expressed breast milk, and directs the milk through a channel 34 to the milk collection container 36.

While the invention is for supporting the breast shield in place, in many if not most instances this will also require supporting the entirety of the breast pump (i.e. parts 32, 34 and 36 and related elements). Since the container 36 may carry on the order of 5 ounces of milk when full, the supporting device should be able to carry the weight of the pump and full container comfortably and with the breast shield properly positioned throughout breast pumping.

A vacuum source 38 communicates with the breast shield 32 and the channel 34 through tubing 39, and creates the suction action in the breast shield 32 that expresses the breast milk from the breast 14. The vacuum source 38 comprises an electric motor-driven breast pump vacuum source for generating an intermittent vacuum. Furthermore, two breast shields 32 may be connected to the vacuum source for simultaneous "double-pumping" of both breasts 14. Other vacuum sources can of course be used with the present invention, such as a battery-driven pump, a manually operated hand-driven piston pump or a squeeze bulb type pump. The latter two are not considered to be particularly advantageous with the present invention, however, since one or both hands may be occupied with operating the manual pumps. For a more detailed description of motor-driven, battery-driven and manually-operated breast pumps, reference may be had to U.S. Pat. Nos. 4,857,051, 4,964,851 and 5,007,899.

Figure 3:
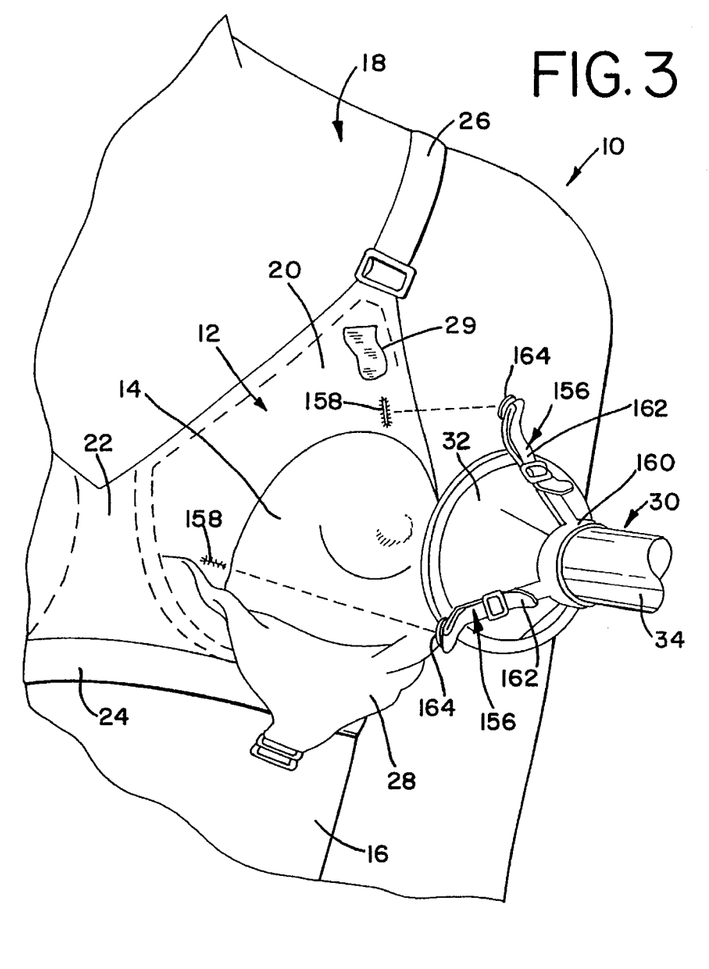
FIG. 3 is an exploded perspective view of a first embodiment of a breast shield support of the present invention.

FIG. 3 shows a first embodiment of the present invention. As shown in FIG. 3, the breast shield support includes a brassiere 12 and a breast pump 30. The breast shield 32 is connected to the brassiere 12 and supported on the breast 14 by a plurality of fasteners in the embodiments shown in FIG. 3 through FIG. 7. The fasteners each include a fastener element disposed on the breast cup 20 of the brassiere 12 and a corresponding mating fastener element associated with the breast shield 32. The corresponding fastener elements are fastened together to attach the breast shield 32 to the brassiere 12 and to thereby support the breast shield 32 on the breast 14 in a "hands-free" fashion.

In FIG. 3, the fastener elements on the brassiere cup 20 are shown to comprise buttonholes 158, and the mating fastener elements 156 on the breast shield 32 are shown to comprise a harness with a support strap 160 having a number of adjustable straps 162 connected to and extending therefrom. The straps 162 include buttons 164 at their ends for insertion in the buttonholes 158. The harness is releasably attached to the breast shield 32 by sliding it over the tubular portion 34 into place or by fastening the support strap 60 around the tubular portion (using some commonplace means to interconnect the ends of the strap 160, not shown herein). No modification of an existing breast pump would therefore be required for use of the harness. Alternately, however, a number of different fasteners may be used to connect the breast shield 32 to the brassiere 12 and to support the breast shield 32 on the breast 14, including for example: a zipper fastener, a slit/double-back strap fastener, a buckle/strap fastener, a garter belt fastener, a magnetic fastener, a snap fastener, a re-usable adhesive tape fastener, a Velcro (i.e., hook-and-loop) fastener, and a hook fastener.

Figure 4:
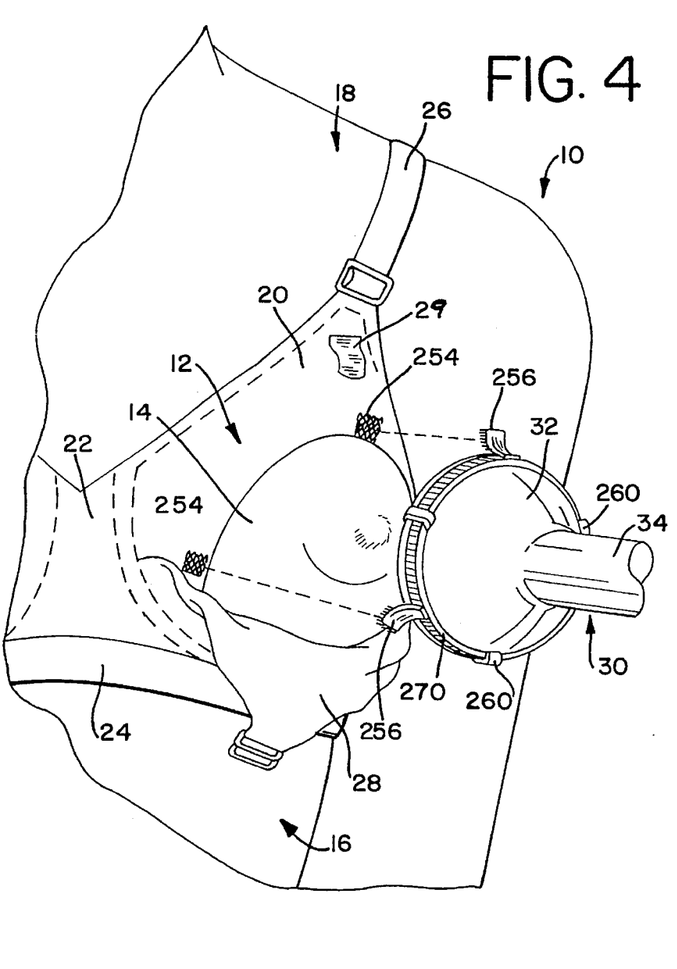
FIG. 4 is an exploded perspective view of a second embodiment of a breast shield support of the present invention.

FIG. 4 shows a second embodiment of the present invention. The breast shield support is very similar to that shown in FIG. 3. The fastener elements 254, 256, however, are connected to a band 270 disposed around the peripheral edge of the breast shield 32. The band 270 may be formed from an elastic material. The band 270 is held in place by friction/interference fit, or as here, by hooks 260. In FIG. 4, the corresponding fastener elements 254, 256 are shown to comprise mating Velcro fasteners. As stated above, however, any suitable type of fastening element may be used.

Figure 5:
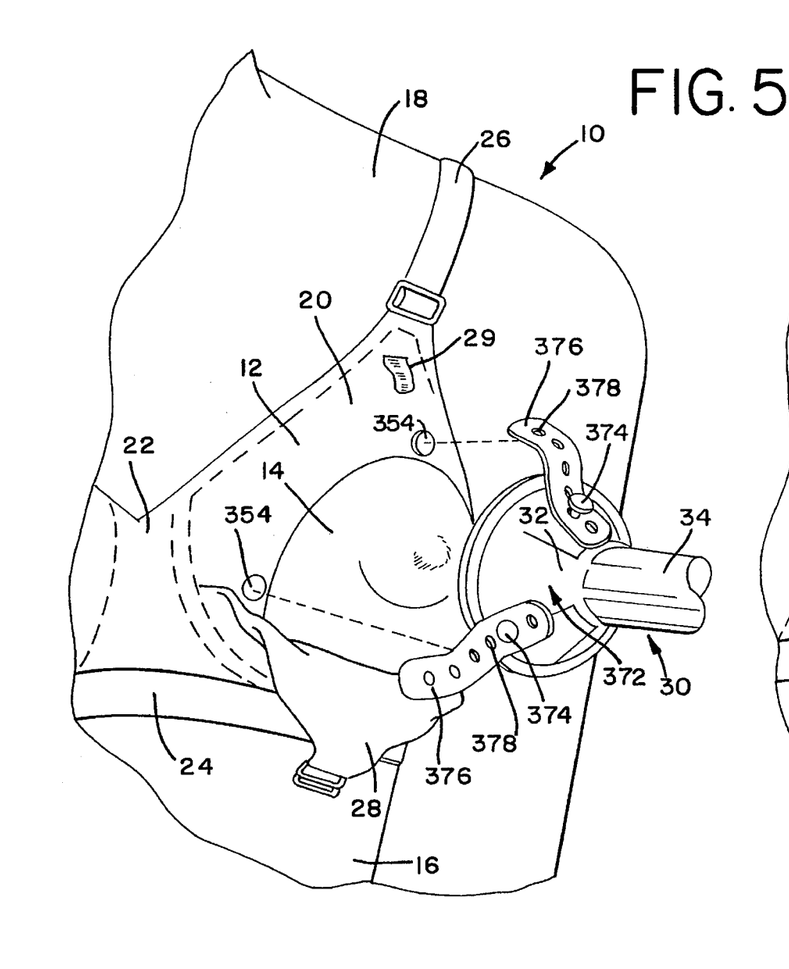
FIG. 5 is an exploded perspective view of a third embodiment of a breast shield support of the present invention.

FIG. 5 shows a third embodiment of the present invention. Again, the breast shield support shown in FIG. 5 is very similar in construction to those shown in FIGS. 3 and 4. One difference, however, is that the fastener elements located on the breast shield 32 are connected to a middle region 372 of the breast shield 32. In the embodiment shown in FIG. 5, the fastener elements comprise studs or rivets 374 formed on or connected to the breast shield 32 and studs or rivets 354 connected to the brassiere cup. Adjustable straps 376 complete the fastener, and each contain a plurality of holes 378 to fit over the rivets 354, 374 to allow the fit of the breast shield 32 on the breast 14 to be adjusted.

Figure 6:
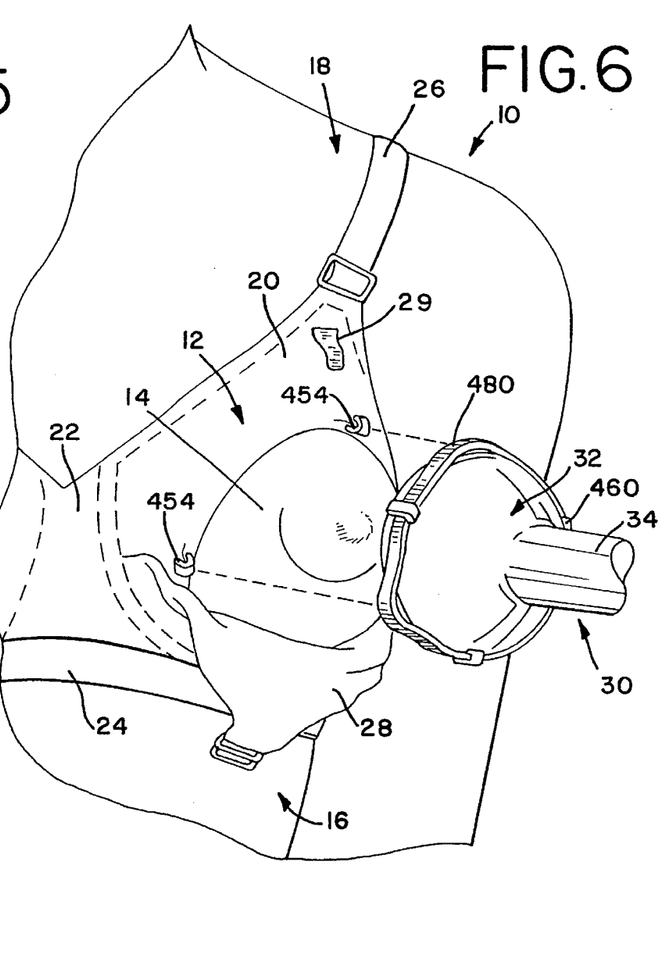
FIG. 6 is an exploded perspective view of a fourth embodiment of a breast shield support of the present invention.

FIG. 6 shows a fourth embodiment of the present invention. In this embodiment, the fastener elements on the brassiere 12 comprise hooks 454, and the fastener elements located on the breast shield 32 comprise an elastic band 480 held in place by hooks 460. The elastic band 480 is disposed around the peripheral edge of the breast shield 32, and may be manipulated to fit around the hook fastener elements 454 to support the breast shield 32 on the breast 14.

It should be understood that the arrangement of the fastener elements shown in FIGS. 3–6 may be interchanged on the brassiere 12 and the breast shield 32, and the number increased or decreased as desired. The kind of fastener used is not limited, although those described herein are considered to be the most advantageous. Also, the fastening elements may be placed at any suitable location on the brassiere 12 or the breast shield 32. Furthermore, the fastening elements located on the breast shield 32 may be connected to any other suitable location on the breast pump 30.

Figure 7:
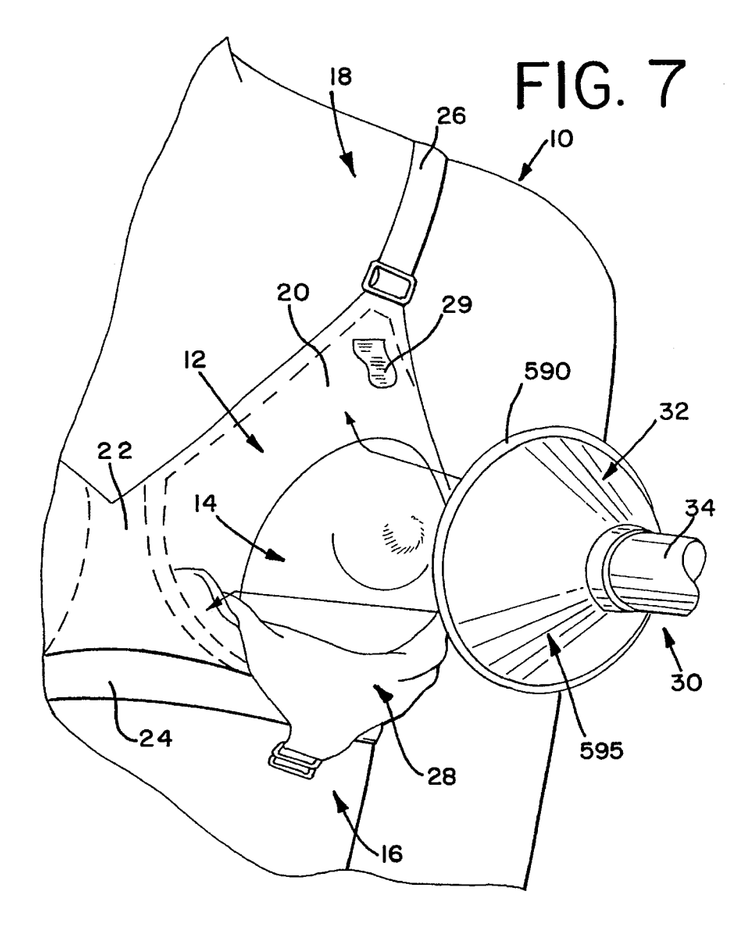
FIG. 7 is an exploded perspective view of a fifth embodiment of a breast shield support of the present invention.

As shown in FIG. 7, a fifth embodiment of the present invention includes a breast shield 32 that is slidably inserted through the flap 28 of the brassiere 12. This breast shield 32 is relatively flexible, such that it contracts about the breast under vacuum. The diameters of the breast shield and the flap opening are sized such that after insertion through the flap 28, the breast shield 32 is supported on the breast 14 between the breast 14 and the inside surface of the breast cup 20 of the brassiere 12. That is, a portion of the flap 28 (i.e., near the bottom of the breast 14), the breast cup 20 material surrounding the exposed portion of the breast 14, and the stiffened peripheral edge 590 of the breast shield 32 cooperate to support the breast shield 32 on the breast 14.

Figure 8:
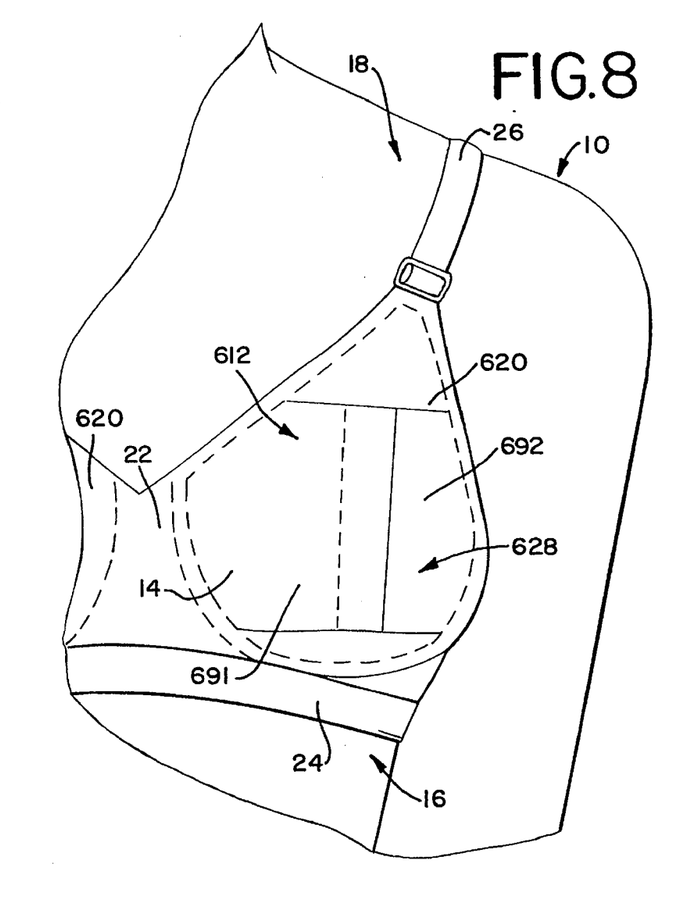
FIG. 8 is an exploded perspective view of a sixth embodiment of a breast shield support of the present invention.

In FIG. 8, which illustrates a variation on the embodiment of FIG. 7, a flap 628 comprises two overlapping sections 691, 692 (similar to those found in mens' briefs), each of which is connected to the breast cup 620 of the brassiere 612. The breast shield (not shown) is supported on the breast 14 by first inserting the breast shield past one section 691 of the flap 628, and then sliding it past and beneath the other section 692. The sections 691, 692 of the flap 628, the breast cup 620 material, and the breast shield (not shown) cooperate to support the breast shield on the breast 14. While the flap 628 shown above is vertically-oriented on the breast cup 620, the flap 628 may be oriented in any suitable direction, including horizontally.

Yet another embodiment of the present invention includes a brassiere 12 having a construction very similar to that shown in FIG. 7. The brassiere 12 shown in FIG. 9, however, includes a flange 793 of semi-rigid material that is disposed at the bottom of the breast cup 20 where the flap 28 connects thereto. When the breast shield 32 is inserted through the flap 28, as described above with respect to FIG. 7, the flange 793 functions to further support the breast shield 32 on the breast 14.

Figure 9:
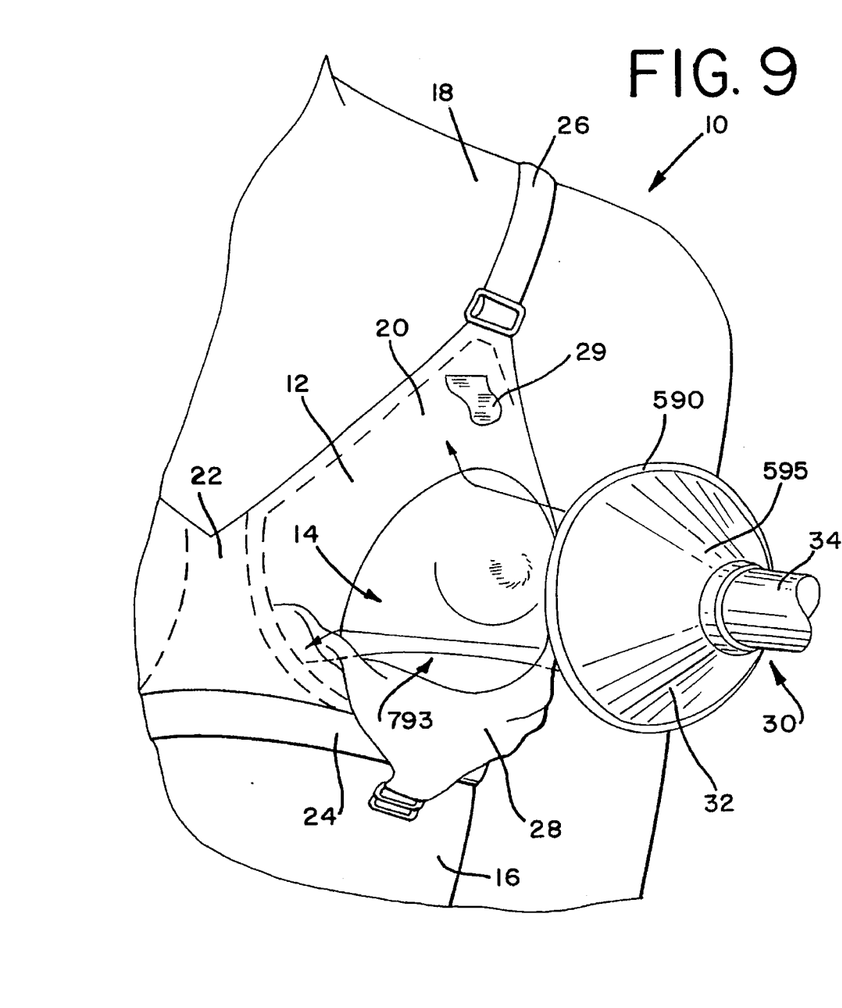
FIG. 9 is an exploded perspective view of a seventh embodiment of a breast shield support of the present invention.

In the embodiments shown in FIGS. 7 and 9, the breast shield 32 of the breast pump 30 may include, as noted, a substantially rigid peripheral edge 590 and a substantially flexible (e.g., "condom-like") interior region 595. The flexible region 595 allows the breast shield 32 to be easily inserted through the flap 28, and to readily conform to the shape of the breast 14. The rigid peripheral edge 590 cooperates with the flap 28 and the inner surface of the breast cup 20 to provide improved support for the breast shield 32 on the breast 14. Conversely, the peripheral edge 590 may be substantially flexible and the interior region 595 may be substantially rigid to support the breast shield 32 on the breast 14.

Figure 10:
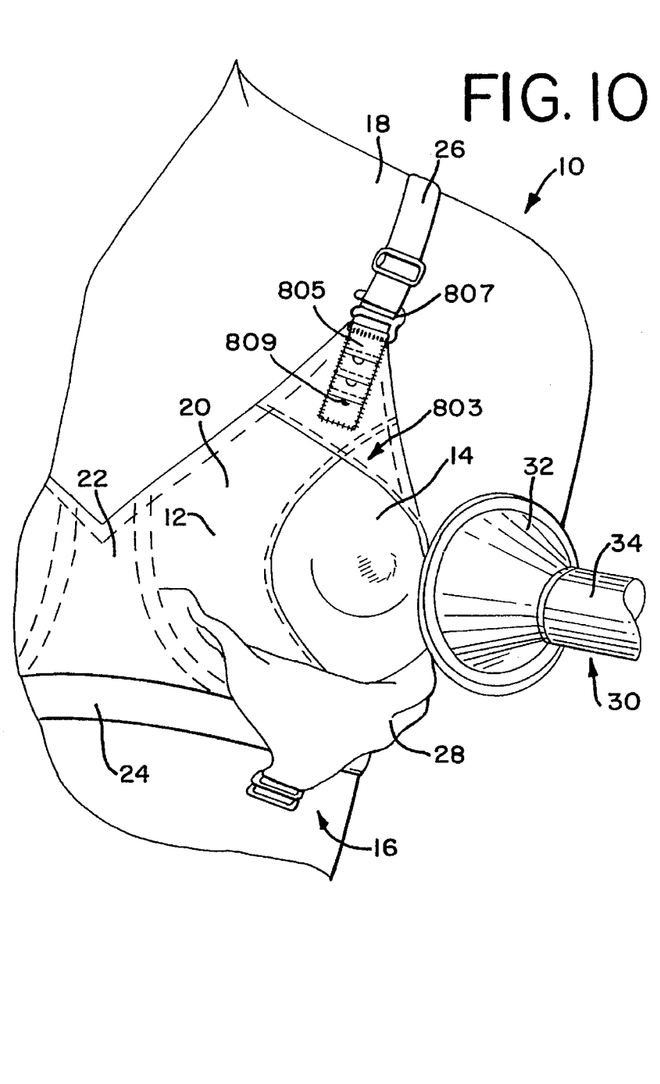
FIG. 10 is an exploded perspective view of an eighth embodiment of a breast shield support of the present invention.

As shown in FIG. 10, an eighth embodiment of the present invention includes a breast cup 20 that is formed with a criss-crossed overlap portion 803. The breast shield 32 is supported on the breast 14 by inserting the breast shield 32 under the criss-crossed overlap 803 and the surrounding breast cup 20 material. The criss-crossed overlap 803, the surrounding breast cup 20 material, and the breast shield 32 cooperate to support the breast shield 32 on the breast 14. The breast cup 20 also includes an adjustable strap 805 attached thereto by, for example, hook-and-eye fasteners 809. The strap 805 is connected to the adjustable shoulder strap 26 via fastening element 807 to support the breast cup 20 against the breast 14. After the breast shield 32 is inserted under the criss-crossed overlap 803 of the breast cup 20, the position of the strap 805 on the breast cup 20 is adjusted via the fasteners 809 to thereby adjust the fit of the breast shield 32 on the breast (i.e., to tighten or loosen the fit of the breast cup 20 on the breast 14).

Figure 11:
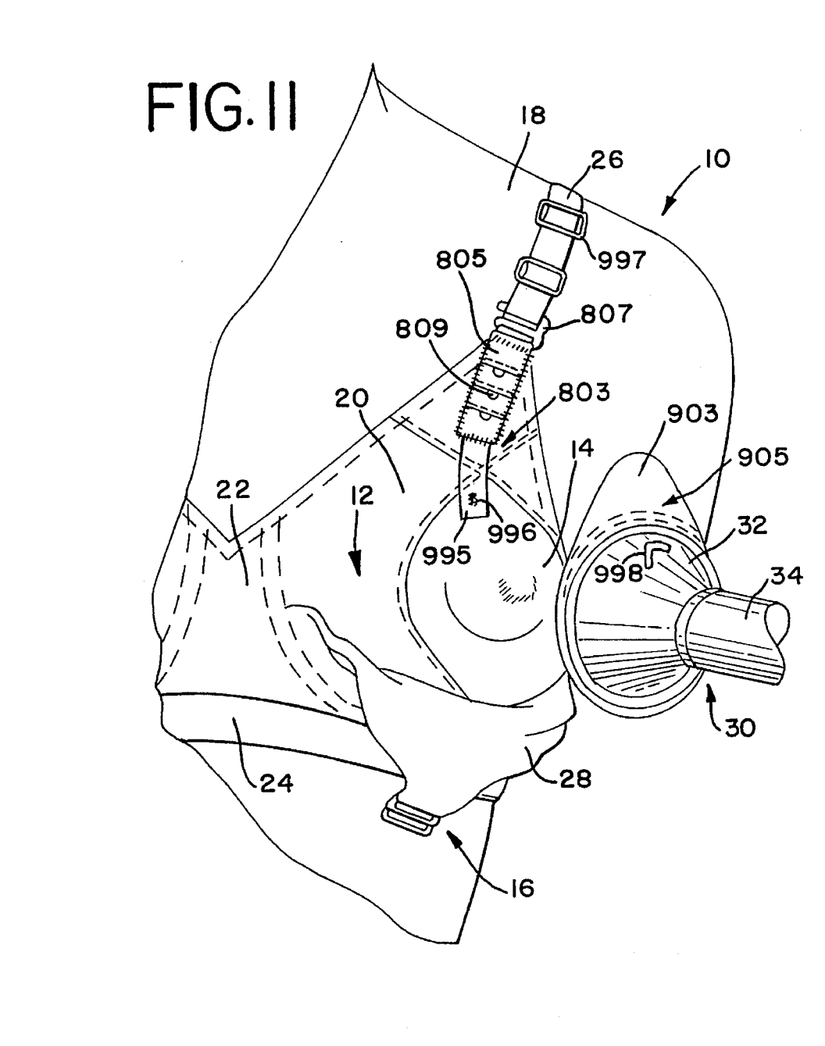
FIG. 11 is an exploded perspective view of a ninth embodiment of a breast shield support of the present invention.
Figure 12:
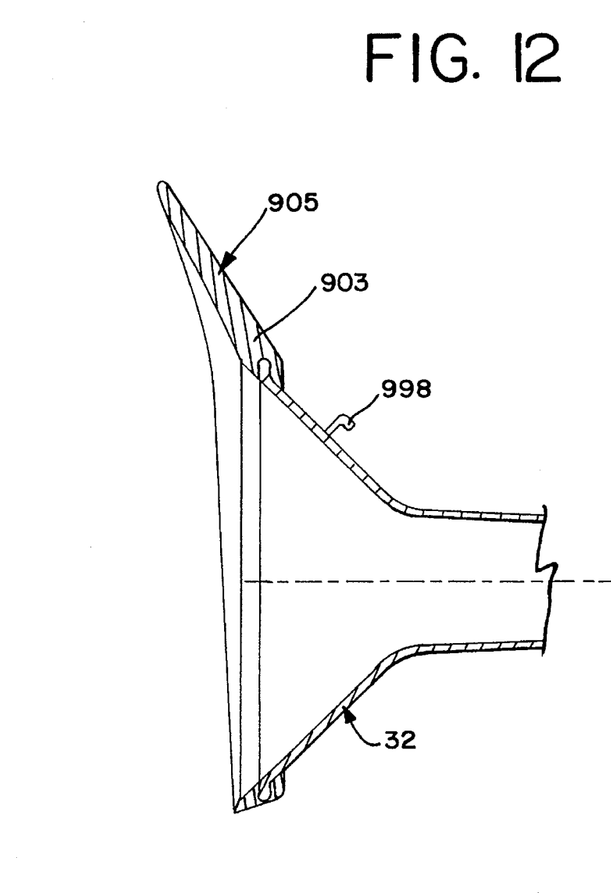
FIG. 12 is a cross-sectional view of the breast shield shown in FIG. 11.

In FIGS. 11 and 12, which illustrate a variation of the embodiment shown in FIG. 10, the breast shield 32 includes a substantially rigid rim 903 disposed around the periphery thereof. The rim 903 is positioned on the breast shield 32 such that a teardrop-shaped portion 905 fits under the criss-crossed overlap 803 when the breast shield 32 is inserted under the criss-crossed overlap 803 and the surrounding breast cup 20 material. The rim 903, and especially the teardrop portion 905 thereof, provides the breast shield 32 with additional surface area, which facilitates supporting the breast shield 32 on the breast 14. The rim 903 is connected to the breast shield 32 by, for example, a "snap" fit, with a bead 904 around the perimeter of the shield fitting into a matching annular recess in the rim 903. In addition, to further support the breast shield 32 on the breast 14, the teardrop portion 905 and the breast cup 20 can be provided with, for example, mating snap-fastening elements (not shown), which are fastened together after the breast shield 32 is inserted under the breast cup 20 material.

In a variation of the embodiment shown in FIGS. 11 and 12, to further support the breast shield 32 on the breast 14, the brassiere 12 may include an additional adjustable support strap 995 connected to the shoulder strap 26. The support strap 995 may be positioned underneath the breast cup 20 of the brassiere 12, from where it may be extracted when needed. The support strap 995 includes a button-hole type opening 996 therein and is adjustably connected to the shoulder strap 26 by means of a buckle 997. A hook 998 may be molded or connected to the breast shield 32 or the rim 903 in any suitable fashion. After the breast shield 32 is inserted under the criss-crossed overlap 803, the support strap 995 may be attached to the hook 998 to further support the breast shield 32. Of course, the support strap 995 may then be adjusted to adjust the fit of the breast shield 32 on the breast 14.

Figure 13:
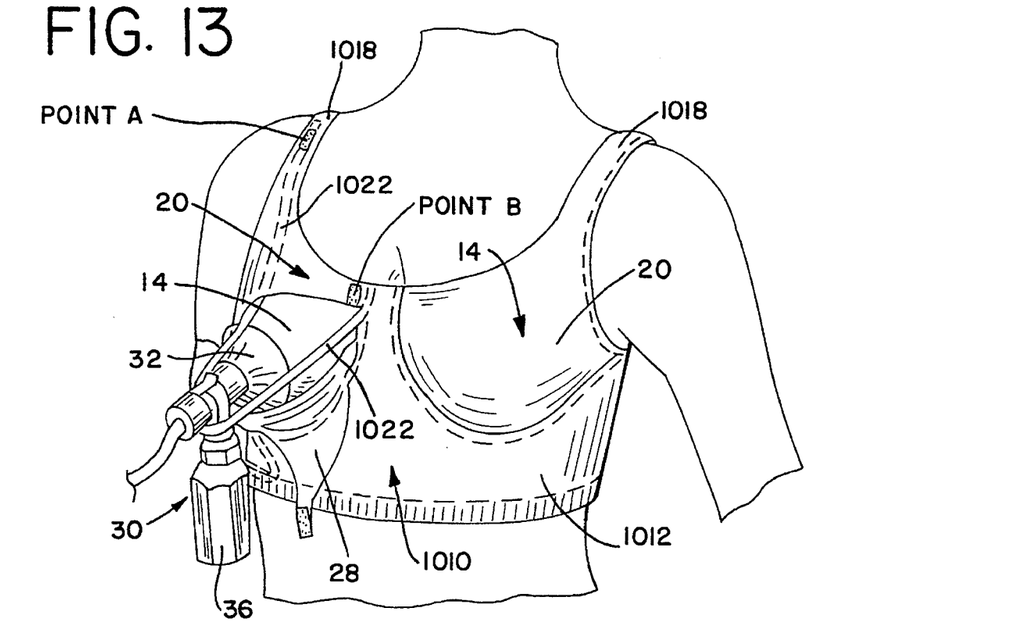
FIG. 13 is an operational view of an tenth embodiment of a breast shield support of the present invention.
Figure 14:
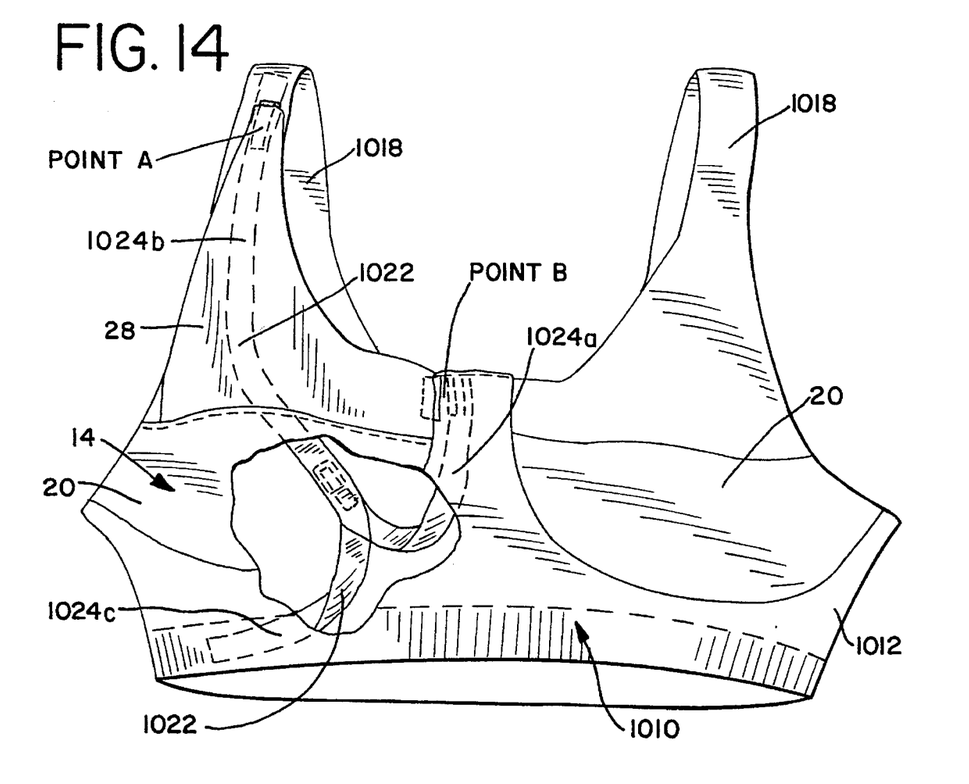
FIG. 14 is an elevational view, partially in cutaway section, of the tenth embodiment shown in FIG. 13.

FIGS. 13 and 14 depict a tenth embodiment of the present invention. A halter top garment 1010—such as a female runner's top-includes includes a band 1012 adapted to fit around a woman's torso, two breast cups 20 connected to the band 1012 and adapted to conform to a woman's breasts 14, and two shoulder straps 1018 each connected between the band 1012 and the breast cups 20, and adapted to go around the woman's shoulders in brassiere fashion.

The garment 1010 includes a flap 28 operable to expose the woman's breast 14 for nursing or breast pumping. The flap 28 is connected to the garment 1010 along the bottom of the breast cup 20, and is detachably connected to the garment 1010 at the shoulder strap 1018 (Point A) and at the top of the breast cup 20 (Point B). In this arrangement, the flap 28 operates to expose the breast 14 as it is moved from the shoulder strap 1018 to the bottom of the garment 1010. Alternately, however, the flap 28 may be oriented on the garment 1010 to expose the breast 14 in any suitable manner. In this embodiment, the flap 28 is connected to the garment 1010 by a Velcro fastener. Again, any suitable type of fastener may be used.

As shown in FIG. 14, the garment 1010 includes a strap 1022 connected to the inner surface of the garment 1010. The strap 1022 is located substantially behind the breast cup 20. The strap 1022 includes three legs or parts 1024a–1024c, each of which is attached to the garment at different locations.

When breast pumping is desired, the flap 28 is unfastened from the garment 1010 to expose the breast 14. The strap 1022 is withdrawn from the interior of the garment 1010 such that it extends through the opening created by the flap 28. The breast pump 30 is placed near the breast 14, and the strap 1022 is extended and fitted around the breast pump 30 such that the strap 1022 presses and supports the breast shield 32 against the breast 14. This is done by taking the loop formed by strap parts 1024a and 1024b and placing that loop under the rearward portion of the breast pump 30 and behind the downwardly extending portion connecting with the bottle 36 (FIG. 13). Strap part 1024c serves to anchor the foregoing loop in position. The strap parts 1024a–1024c are then adjusted to ensure that the breast shield 32 fits snugly, but not uncomfortably, against the breast 14. Adjustment may be accomplished by providing an elastic strap 1022, and/or adjustable extenders at points of interconnection.

Figure 16:
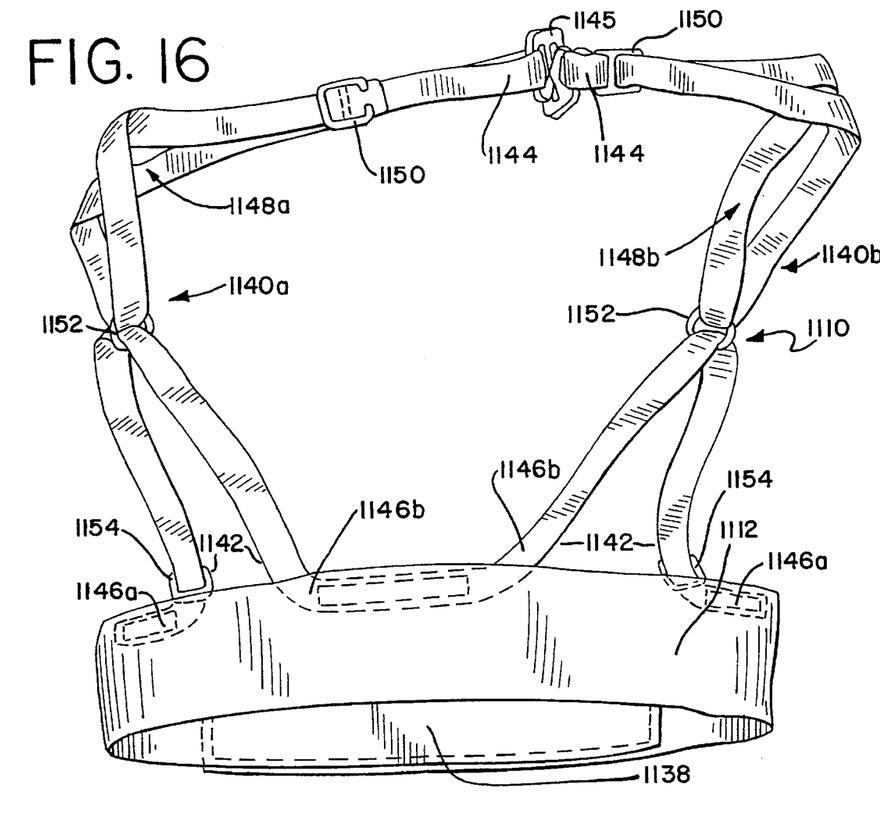
FIG. 16 is an elevational view of the eleventh embodiment shown in FIG. 15.

FIGS. 15 and 16 depict an eleventh embodiment of the present invention. This harness garment 1110 includes a band 1112 adapted to fit around the torso and two adjustable strap arrangements 1140a, 1140b for each breast 14. The band 1112 has two ends that are connected together at the woman's back by, for example, a Velcro fastener 1138. The straps 1140a, 1140b each have first ends 1142 connected to the band 1112 and second ends 1144 connectable to each other at hook fastener 1145. As shown in FIG. 15, the second ends 1144 are connected together behind the woman's neck. Alternately, the seconds ends 1144 are connected to brassiere shoulder straps (not shown). In addition, and as shown in FIG. 16, the first ends 1142 of each strap 1140a, 1140b include two legs or parts 1146a, 1146b that are connected to the band 1112, as by sewing. The two legs 1146a, 1146b of the respective ends 1142 are spaced apart on the band 1112, and are here formed from a continuous piece of material in a pair of loops.

The straps 1140a, 1140b include two closed breast loops 1148a, 1148b that are adapted to rest or press against the breast 14. As shown in FIG. 15, the breast loops 1148a, 1148b are each sized to fit around and to hold a breast shield 32 on an exposed breast 14. Each breast loop 1148a, 1148b is connected to a respective pair of legs 1146a, 1146b (each pair forming a loop) via a ring connector 1152.

In use, the breast pump 30 is placed near a respective breast loop, such as loop 1148a, and the loop 1148a is extended and fitted around the breast pump 30 in the manner previously described with respect to the tenth embodiment, such that the loop 1148a presses and supports the breast shield 32 against the breast 14. The strap 1140a, and thus the loop 1148a, is then adjusted, via an adjusting buckle 1150, to ensure that the breast shield 32 fits tightly against the breast 14. A similar buckle 1154 on each leg 1146a allows adjustment of the loops formed by legs 1146a, 1146b.

When "double-pumping" is desired, as shown in FIG. 15, each breast loop 1148a, 1148b is extended and fitted around a separate breast pump 30 to support the breast shields 32 on the breasts 14.

While the tenth and eleventh embodiments of the present invention have been shown and described above in terms of a halter and a harness garment 1010, 1110, it is specifically contemplated that any suitable type of garment may be used with the present invention, including standard brassieres, strapless brassieres, camisoles, and tank tops, to name a few. Furthermore, the harness and halter top garments 1010, 1110, including the straps 1022, 1140a, 1140b, may be formed of any suitable elastic or other material.

Figure 17:
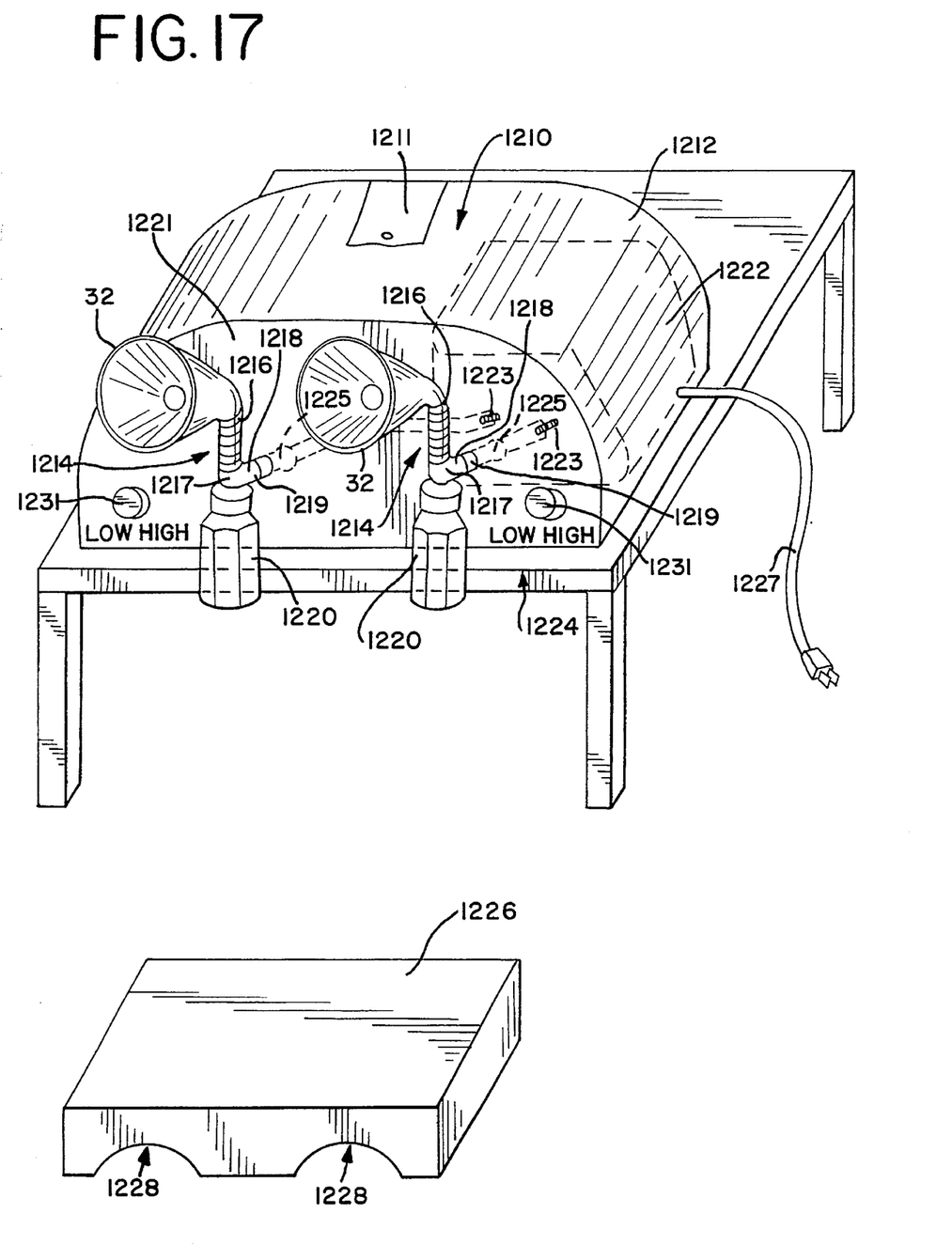
FIG. 17 is a perspective view of a twelfth embodiment of a breast shield support of the present invention.

FIG. 17 depicts a twelfth embodiment of the present invention. The breast shield support 1210 includes a base member 1212 to which two breast shields 32 are connected by air tubes 1214, each of which has a flexible portion 1216 and a rigid portion 1218. The rigid portions 1218 of the air tubes 1214 hold the breast shields 32 up and away from the base member 1212, and the flexible portions 1216 allow a woman to adjust the breast shields 32 on her breasts to insure a tight yet comfortable fit.

The air tube 1214 of each breast shield 32 is connected via a conventional coupling arrangement to a milk collection container 1220 located externally of the base member 1212. Alternately, the collection containers 1220 may be located inside of the base member 1212.

As explained below, the air tubes 1214 connect a vacuum source 1222 located in the base member 1212 to the breast shields 32 to produce the suction action in the breast shields 32. The breast milk expressed from the breasts during breast pumping is collected in the collection containers 1220. After breast pumping is completed, the collection containers 1220 are disconnected from the air tubes 1214, and the breast milk is removed for storage.

As described in U.S. Pat. No. 4,929,229, the breast shields 32 each include an internal baffle and a valve. The baffle and valve cooperate to direct breast milk through the air tube 1214 and into the collection container 1220, thus preventing the breast milk from being drawn into that portion of the air tube 1214 extending past the collection container 1220 and into the base member 1212.

A coupling 1219 connects the rigid portion 1218 of each air tube 1214 to the base member 1212 to hold the breast shields 32 in place. The air tubes 1214 pass through a front wall 1221 of the base member 1212 and terminate at a vacuum source 1222. The air tubes 1214 are connected to the vacuum source 1222 by conventional connectors 1223. The couplings 1219 and the connectors 1223 allow a user to disconnect the air tubes 1214 and the breast shields 32 from the breast shield support 1210 for cleaning, repair and/or replacement. Access to the interior of the breast shield support 1210 is provided by a panel 1211.

Each of the air tubes 1214 includes a liquid and/or bacterial filter 1225. The liquid filter prevents breast milk or other liquid from passing through the air tubes 1214 and damaging the vacuum source 1222. The bacterial filter prevents the expressed breast milk from being contaminated by bacteria that may be present in the air tubes 1214 and the vacuum source 1222.

The breast shield support 1210 includes an electrical power cord 1227 connected to the vacuum source 1222. The power cord 1227 is connected to a power source (not shown) to drive the vacuum source 1222. The breast shield support 1210 may also include a battery for powering the vacuum source when an external electrical power source is not readily available or when the power supply has been interrupted.

The base member 1212 includes two vacuum control knobs 1231 associated with the vacuum source 1222. The control knobs 1231 may be manipulated to increase or decrease the suction produced in the respective breast shields 32 by the vacuum source 1222.

In an alternate embodiment, a cradle-like device (not shown) may be attached to the base member 1212 by a flexible and/or pivotable support arm (not shown). A breast shield 32 and tubing as shown in FIG. 13 may be held in the cradle-like device and supported against a woman's breasts for breast pumping.

The base member 1212 may be supported atop a table 1224, and a woman may sit or stand next to the base member 1212 and position the breast shields 32 against her breasts for hands-free "double pumping."

A lap support 1226 having recessed areas 1228 to accommodate a user's legs may be used instead of the table 1224 to support the breast shield support 1210. A woman who desires to breast pump while sitting may position the lap support 1226 on her lap, and rest the breast shield support 1210 on the lap support 1226. The breast shields 32 are then manipulated into position on the breasts for breast pumping.

Figure 18:
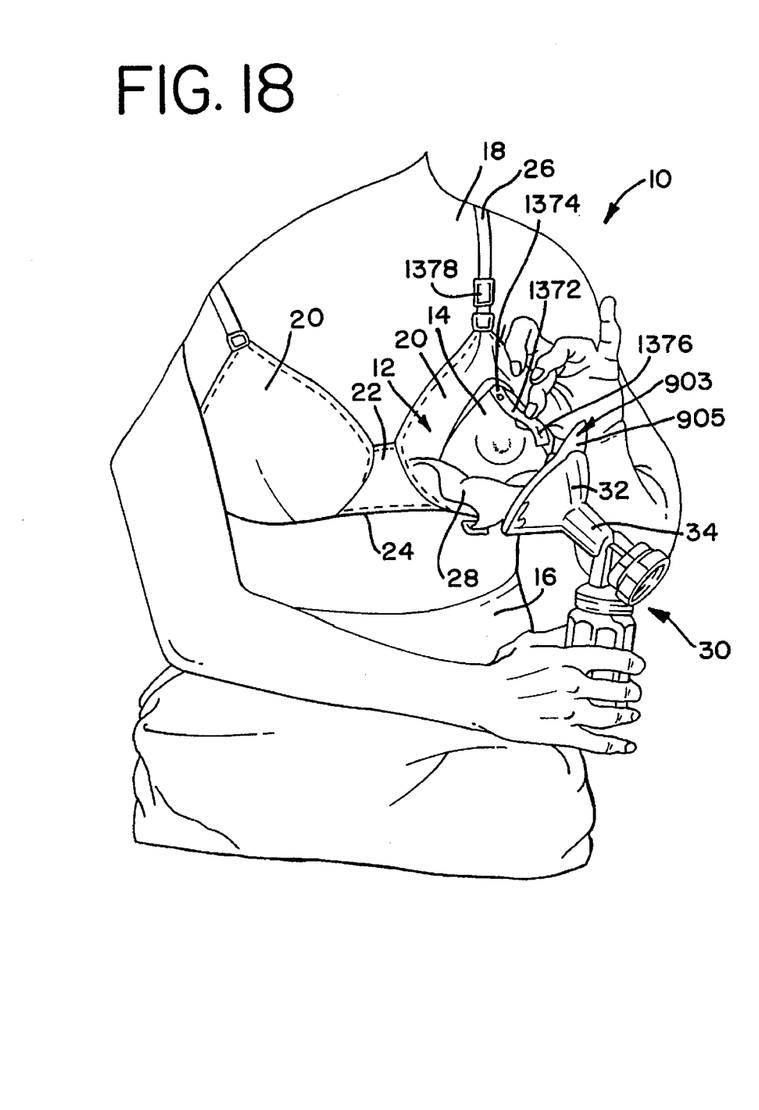
FIG. 18 is an exploded perspective view of a thirteenth embodiment of a breast shield support of the present invention.
Figure 19:
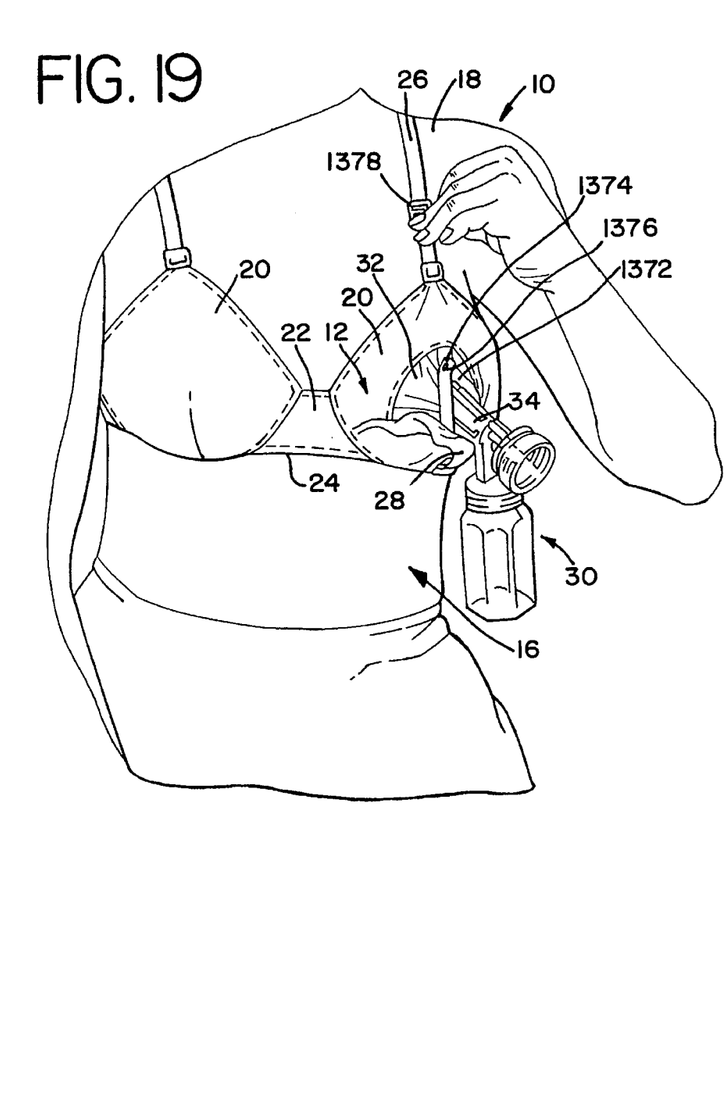
FIG. 19 is an operational view of the thirteenth embodiment shown in FIG. 18.

FIGS. 18 and 19 depict a thirteenth embodiment of the present invention, which is a variation of the embodiment shown in FIGS. 11 and 12. As shown, the brassiere 12 may include an adjustable support strap 1372 connected to the shoulder strap 26. The support strap 1372 may be positioned underneath the breast cup 20 of the brassiere 12, from where it may be extracted when needed. The support strap 1372 includes a button 1374 and a button-hole type opening 1376 spaced therealong, and is adjustably connected to the shoulder strap 26 by means of a buckle 1378. After the breast shield 32 is inserted under the breast cup 20, the support strap 1372 is extended around the breast shield channel 34 and attached to itself (via the button 1374 and button hole 1376) to support the breast shield 32 on the breast 14. Of course, as shown in FIG. 19, the support strap 1372 may then be adjusted (via the buckle 1378) to adjust the fit of the breast shield 32 on the breast 14.

In an alternate embodiment, the support strap 1372 may be formed into a loop, thereby eliminating the need for the button 1374 and the button hole 1376. Further, the support strap 1372 may be elasticized. Additionally, instead of the button 1374 and button hole 1376 arrangement, any other suitable types of fasteners may be used.

As stated above, the present invention permits a nursing mother to use a breast pump to collect and store breast milk, while also providing her with free use of her hands to perform other job tasks or chores. In addition, the present invention allows for hands-free "double pumping." Further, the present invention is simple to use and allows the breast shield to be quickly supported on the exposed breast.

It should be appreciated that the present invention may be modified or configured as appropriate for the application. The embodiments described above are to be considered in all respects only as illustrative and not restrictive. Changes may be made without departing from the spirit of the invention. The scope of the invention is indicated by the following claims rather than by the foregoing description. All changes which come within the literal meaning as well as the range of equivalency of the claims are to be embraced within their scope.

What is claimed is:

1. A device for supporting a breast shield on a breast comprising:

a base; and means for supporting the breast shield on the breast which means is carried by said base.

2. The device of claim 1 wherein said breast shield is part of a breast pump assembly, and said means for supporting comprises a strap connected to said base which strap is engaged with a portion of said breast pump assembly including the breast shield, and positions the breast shield on the breast.

3. A device for supporting a breast shield of a breast pump on a breast comprising:

a base member adapted to be carried on a human body; and means for affixing a part of the breast pump to said base member such that the breast shield is supported on the breast.

4. The device of claim 3 wherein said base member comprises a garment having means for exposing the breast.

5. The device of claim 4 wherein said means for exposing comprises a flap, and further wherein said means for affixing comprises an aperture formed by said flap which has a smaller effective diameter than the breast shield, whereby an inner surface area of said garment surrounding said aperture overlies the breast shield and holds the breast shield pressed against the breast.

6. The device of claim 3 wherein said means for affixing comprises first and second corresponding fastener elements, said first fastener element being disposed on said base member and said second fastener element being disposed on a part of the breast pump, whereby said first and second corresponding fastener elements are fastened together to support the breast shield on the exposed breast.

7. The device of claim 6 wherein said second fastener element is disposed on the breast shield.

8. A breast pump support device, wherein said breast pump includes a breast shield adapted to receive a breast therein for expressing milk, comprising:

a garment adapted to be worn around a woman's torso; and means for fastening a breast pump to said garment such that a breast shield is supported on an exposed breast.

9. The breast pump support device of claim 8 wherein said garment comprises a brassiere with two breast cups, said means for fastening comprises a flap in material forming a cup which is operable to expose at least the nipple and adjacent breast area of one of the woman's breasts, and which flap defines an aperture through which the breast shield passes, with material forming said cup overlying the breast shield after passing through said aperture such that said overlying material holds the breast shield in place on the breast.

10. The breast pump support device of claim 9 further comprising a respective flap for each breast cup formed on said garment.

11. The breast pump support device of claim 9 wherein said aperture is formed by a first section connected to a cup, and a second section connected to a cup in overlapping relationship with said first section, whereby said first and second sections may be manipulated past one another to form an opening in said cup to expose the breast.

12. The breast pump support device of claim 11 wherein said opening is vertically oriented on said cup.

13. The breast pump support device of claim 9 wherein the breast shield comprises:

a flexible portion that is deformable to conform to the shape of the exposed breast; and a rigidified peripheral edge that is operable to support the breast shield on the exposed breast between the exposed breast and said overlying material.

14. The breast pump support device of claim 9 wherein the breast shield comprises:

a flexible peripheral edge portion that is deformable to permit the insertion of the breast shield through said flap and to conform to the shape of the exposed breast; and a rigidified portion inboard from said flexible peripheral edge portion that is operable to support the breast shield on the exposed breast between the exposed breast and the inner surface of said garment.

15. The breast pump support device of claim 8 wherein said means for fastening comprises first and second corresponding fastener elements, said first fastener element being disposed on said garment and said second fastener element being disposed on a part of the breast pump, whereby said first and second corresponding fastener elements are fastened together to support the breast shield on the exposed breast.

16. A breast pump assembly wherein the breast shield is maintained positioned over a breast without need of any manual force, comprising:

a base member adapted to be carried on a woman's body;

a breast pump including at least one breast shield adapted to be received over a breast nipple and adjacent breast area, and a container for expressed milk in fluid communication with said breast shield;

means for generating an intermittent vacuum in said breast shield to thereby express milk; and means for affixing a part of said breast pump to said base member with said breast shield supported over the nipple and adjacent breast area.

17. The breast pump assembly of claim 16 wherein said means for affixing comprises first and second corresponding fastener elements, said first fastener element being disposed on said base member and said second fastener element being disposed on said breast shield, whereby said first and second corresponding fastener elements are releasably fastened together to support said breast shield on the exposed breast.

18. The breast pump assembly of claim 17 wherein said second fastener element comprises a band positioned around the peripheral edge of said breast shield, said band having a fastener element member disposed on the band.

19. The breast pump assembly of claim 16 wherein said base member comprises a garment having at least one detachable flap operable to cover and to expose the breast.

20. The breast pump assembly of claim 16 wherein said base member comprises a garment having two detachable flaps, each of said flaps being operable to expose a respective breast.

21. The breast pump assembly of claim 20 wherein said garment comprises a brassiere.

22. The breast pump assembly of claim 16 wherein said means for affixing comprises a button/buttonhole fastener.

23. The breast pump assembly of claim 16 wherein said means for affixing comprises a hook-and-loop fastener.

24. The breast pump assembly of claim 16 wherein said means for affixing comprises a buckle/belt fastener.

25. The breast pump assembly of claim 16 wherein said means for affixing comprises a garter belt fastener.

26. The breast pump assembly of claim 16 wherein said means for affixing comprises a magnetic fastener.

27. The breast pump assembly of claim 16 wherein said means for affixing comprises a snap fastener.

28. The breast pump assembly of claim 16 wherein said means for affixing comprises a re-usable adhesive tape fastener.

29. The breast pump assembly of claim 16 wherein said means for affixing comprises a zipper fastener.

30. The breast pump assembly of claim 16 wherein said means for affixing comprises a hook positioned on said base member and an elastic band positioned around the peripheral edge of said breast shield.

31. The breast pump assembly of claim 16 wherein said means for affixing comprises a button/adjustable strap fastener, the adjustable strap comprising a plurality of holes, each of the holes being sized to accommodate the button.

32. A method for supporting a breast shield on a breast, comprising the following steps:

providing a base member;

providing affixation means for mounting the breast shield to said base member; and mounting the breast shield to said base member using said affixation means such that the breast shield is supported on an exposed breast.

33. The method of claim 32 wherein said base member comprises a brassiere-type garment having a bra cup with a detachable flap for exposing the breast.

34. The method of claim 33 wherein the step of mounting comprises sliding the breast shield through said flap with material of said bra cup holding the breast shield in place upon the breast.

35. The method of claim 32 wherein said affixation means comprises first and second corresponding fastener elements, said first fastener element being disposed on said base member and said second fastener element being disposed on part of a breast pump, whereby said mounting step comprises fastening said first and second corresponding fastener elements together to support the breast shield on the exposed breast.

36. The method of claim 35 wherein said second fastener element is disposed on the breast shield.

37. A device for supporting a breast shield of a breast pump upon a breast comprising:

strap means for supporting the breast shield on the breast; and a garment, said strap means being attached to said garment.

38. The device of claim 37 wherein said strap means comprises a first strap having a loop portion within which loop portion a part of said breast pump is received, said first strap being attached to said garment above the breast, a second strap attached to said loop portion and which second strap is further attached to said garment below the breast, and means to adjust said first and second straps to press the breast shield against the breast.

39. A device for supporting a breast shield upon a breast comprising:

a base member; and a strap connected to said base member, said strap including means for supporting a part of the breast pump with the breast shield on the breast.

40. The device of claim 39 wherein said base member comprises a halter top.

41. The device of claim 40 wherein the halter top includes a breast cup having a flap for exposing the breast.

42. The device of claim 39 wherein said strap has a loop portion adapted to receive and hold the breast shield against the breast.

43. The device of claim 42 wherein said base member comprises a band adapted to conform to a woman's body below the breasts, and a halter portion which extends from a first loop portion on one breast behind the neck of the woman to a second loop portion on the other breast, said loop portions being attached to said halter portion and said band, and means for adjusting said loop portions to press respective breast shields against the breasts.

44. A device for supporting a breast shield upon a breast comprising:

a garment comprising a first base adapted to be carried on a human body below the breast, and a second base adapted to be carried on the body in the area of the shoulders; and a first strap for supporting one breast shield on a breast and a second strap for supporting a second breast shield on another breast, each of said first and second straps including a loop portion adapted to receive and hold the breast shield against the exposed breast, each said loop portion being attached to said second base, and auxiliary strap portions respectively connecting respective loop portions to said first base.

45. The device of claim 44 wherein garment is a brassiere-type garment having breast cups, said first and second straps and said auxiliary strap portions are connected to an inside surface of said brassiere-type garment and are accessible through a flap formed on each breast cup.

46. The device of claim 44 further including means for adjusting each of said first and second straps so that said first and second straps press said breast shields against the breasts.

47. The device of claim 45 wherein said garment comprises a halter top.

48. A breast pump assembly including a device for supporting a breast shield on a breast comprising:

two breast pumps each having a breast shield within which a breast is received for expressing milk, and a container in fluid communication with said breast shield for receiving expressed milk;

means for generating an intermittent vacuum in said breast shields to express milk; and a strap arrangement for supporting said breast shields on the breasts, said strap arrangement including a first loop portion adapted to receive and hold one breast shield against a breast, a halter portion which extends from said first loop portion on one breast to a second loop portion adapted to receive and hold the other breast shield against the other breast, and auxiliary portions respectively connecting said first and second loop portions to a band adapted to be worn below the breasts.

49. The breast pump assembly of claim 48 wherein each of said auxiliary portions have a first end and a second end, said first and second ends of said auxiliary portions being connected to said band, and an intermediate part of said auxiliary portions between said first and second ends being connected to a respective loop portion.

50. The breast pump assembly of claim 49 wherein each of said loop portions have upper loop ends which are attached to a halter portion strap which extends behind the woman's neck.

51. The breast pump assembly of claim 48 including means for adjusting said strap arrangement.

52. A method for supporting a breast shield of a breast pump on a woman's breast, comprising the following steps:

provide a garment having a strap arrangement for supporting the breast shield on the breast; and placing said strap arrangement around the breast pump such that said strap holds the breast shield on an exposed breast.

53. The method of claim 52 wherein said strap arrangement includes a loop portion within which a part of the breast pump is received.

54. The method of claim 53 further comprising placing said loop portion under a rearward portion of the breast shield and behind a downwardly extending portion connecting the breast pump with a collection bottle.

55. The method of claim 52, further comprising the additional step of adjusting said strap arrangement to ensure that the breast shield fits snugly against the breast.

* * * * *